US010111904B2

(12) United States Patent
Danscher

(10) Patent No.: US 10,111,904 B2
(45) Date of Patent: Oct. 30, 2018

(54) MICRON-SIZED GOLD, KIT COMPRISING SAID GOLD AND ITS USE AS A NON-TOXIC IMMUNE SUPPRESSOR

(71) Applicant: BERLOCK APS, Aarhus C (DK)

(72) Inventor: Gorm Danscher, Aarhus C (DK)

(73) Assignee: Berlock ApS, Aarhus C (DK)

( * ) Notice: Subject to any disclaimer, the term of this patent is extended or adjusted under 35 U.S.C. 154(b) by 662 days.

(21) Appl. No.: 14/150,297

(22) Filed: Jan. 8, 2014

(65) Prior Publication Data
US 2014/0194852 A1 Jul. 10, 2014

(30) Foreign Application Priority Data
Jan. 9, 2013 (DK) .................................. 2013 70007

(51) Int. Cl.
| | |
|---|---|
| A61K 33/24 | (2006.01) |
| A61K 9/14 | (2006.01) |
| A61L 27/30 | (2006.01) |
| A61L 27/54 | (2006.01) |
| A61K 9/00 | (2006.01) |
| A61K 47/36 | (2006.01) |
| A61L 27/32 | (2006.01) |
| C08L 5/08 | (2006.01) |

(52) U.S. Cl.
CPC ............ *A61K 33/24* (2013.01); *A61K 9/0019* (2013.01); *A61K 9/14* (2013.01); *A61K 47/36* (2013.01); *A61L 27/306* (2013.01); *A61L 27/32* (2013.01); *A61L 27/54* (2013.01); *C08L 5/08* (2013.01); *A61L 2300/102* (2013.01); *A61L 2300/802* (2013.01); *A61L 2400/06* (2013.01); *A61L 2400/12* (2013.01); *A61L 2420/04* (2013.01)

(58) Field of Classification Search
CPC ............... A61L 27/32; A61L 2300/102; A61L 2300/802; A61L 2400/06; A61L 2400/12; A61L 2420/04; A61L 27/306; A61L 27/54; C08L 5/08; A61K 33/24; A61K 47/36; A61K 9/0019; A61K 9/14
USPC ........................ 424/489, 649; 604/506, 93.01
See application file for complete search history.

(56) References Cited

U.S. PATENT DOCUMENTS

| | | | |
|---|---|---|---|
| 6,037,366 A | 3/2000 | Krall et al. | |
| 7,256,183 B2 * | 8/2007 | Peterson | A61K 31/00 514/47 |
| 2006/0286142 A1 * | 12/2006 | Woodbury | A61C 8/0012 424/423 |
| 2008/0050452 A1 * | 2/2008 | Chen | A61K 9/0014 424/618 |
| 2010/0323985 A1 * | 12/2010 | Moutet | A61K 8/63 514/54 |

FOREIGN PATENT DOCUMENTS

| | | |
|---|---|---|
| FR | 1579456 A | 12/1964 |
| FR | 2807657 A1 | 10/2001 |
| WO | 2006056055 A2 | 6/2006 |
| WO | WO 2006056055 A2 * | 6/2006 ............. A61K 33/24 |

OTHER PUBLICATIONS

Aktas, O. et al, Neuronal Damage in Brain Inflammation, Arch Neurol, Feb. 2007, pp. 185-189, vol. 64, American Medical Association.
Aschner, M., et al., Astrocyte Modulation of Neurotoxic Injury, Symposium: Recent Mechanistic and Molecular Concepts in Neurotoxicology, Brain Pathol, 2002; pp. 475-481, vol. 12.
Danscher, G., Localization of Gold in Biological Tissue, A Photochemical Method for Light and Electronmicroscopy, Histochemistry, 1981, pp. 81-88, vol. 71, Springer-Verlag.
Danscher, G., In vivo liberation of gold ions from gold implants. Autometallographic tracing of gold in cells adjacent to metallic gold, Histochemistry and Cell Biology Journal, 2002, pp. 447-452, vol. 117, Springer-Verlag.
Danscher, G. et al., Autometallography (AMG) Silver enhancement of quantum dots resulting from (1) metabolism of toxic metals in animals and humans, (2) in vivo, in vitro and immersion created zinc-sulphur/zinc-selenium nanocrystals, (3) metal ions liberated from metal implants and particles. Progress in Histochemistry and Cytochemistry, 2006, pp. 57-139, vol. 41, Elsevier GmbH.
Felson, D.T. et al., The comparative efficacy and toxicity of second-line drugs in rheumatoid arthritis, Results of Two Metaanalyses, Arthritis & Rheumatism, Official Journal of the American College of Rheumatology, 1990, pp. 134-213, vol. 33, No. 10.
Ferre, N. et al., New insight into the regulation of 30 liver inflammation and oxidative stress, Mini-Reviews in Medicinal Chemistry, 2006, pp. 1321-1330, vol. 6, Bentham Science Publishers Ltd.
Futami, T. et al., Tissue Response to Titanium Implants in the Rat Maxilla: Ultrastructural and Histochemical Observations of the Bone-Titanium Interface, J. Periodontol.,2000, pp. 287-298, vol. 71, No. 2.
Larsen, A. et al., Gold ions bio-released from metallic gold particles reduce inflammation and apoptosis and increase the regenerative responses in focal brain injury, Histochemistry and Cell Biology Journal, 2008, pp. 681-692, vol. 130, Springer-Verlag.
Larsen, A. et al., In vitro liberation of charged gold atoms: autometallographic tracing of gold ions released by macrophages grown on metallic gold surfaces, Histochemistry and Cell Biology Journal, 2007, pp. 1-6, vol. 128, Springer-Verlag.

(Continued)

*Primary Examiner* — Johann R Richter
*Assistant Examiner* — Courtney A Brown
(74) *Attorney, Agent, or Firm* — Sughrue Mion, PLLC

(57) ABSTRACT

Sterile micron-sized gold particles contained in capped vials, a kit of part including the vial and a liquid capable of suspending the particles, as well as their preparation, medical devices or medicaments prepared by their preparation as well as uses thereof in treating inflammation. Also, gold coated implants preferably for use in combination with the medical devices.

13 Claims, No Drawings

(56) References Cited

OTHER PUBLICATIONS

Mhatre, M. et al., Oxidative stress and neuroinflammation in Alzheimer's disease and amyotrophic lateral sclerosis: Common links and potential therapeutic targets. Journal of Alzheimer's Disease, 2004, pp. 147-157, vol. 6, IOS Press and the authors.
Pedersen, M.O. et al., Metallic gold reduces TNFalpha expression, oxidative DNA damage and pro-apoptotic signals after experimental brain injury, Brain Research, 2009, pp. 103-113, vol. 1271, Elsevier B.V.
Pedersen, M.O. et al., Bio-released gold ions modulate expression of neuroprotective and hematopoietic factors after brain injury, Brain Research, 2010, pp. 1-13, vol. 1307, Elsevier B.V.
Pedersen, M.O. et al., Metallic gold treatment reduces proliferation of inflammatory cells, increases expression of VEGF and FGF, and stimulates cell proliferation in the subventricular zone following experimental traumatic brain injury, Histology and Histopathology, 2009, pp. 573-586, vol. 24.
Roach, P. et al., Modern biomaterials: a review-bulk properties and implications of surface modifications, Journal of Material Science: Materials in Medicine, 2007, pp. 1263-1277, vol. 18, Springer Science+Business Media, LLC.
Zainali, K. et al., Assessment of modified gold surfaced titanium implants on skeletal fixation, Journal of Biomedical Materials Research Part A, 2012, pp. 195-202, vol. 101, Issue 1, Wiley Periodicals, Inc.
Persellin, R.H. et al., The Effect of Gold Salt on Lysosomal Enzymes of the Peritoneal Macrophage, Arthritis and Rheumatism, 1966, pp. 57-65, vol. 9, No. 1.
Potashkin, J.A. et al., The Role of Oxidative Stress in the Dysregulation of Gene Expression and Protein Metabolism in Neurodegenerative Disease, Antoxididants & Redox Signaling, 2006, pp. 144-151, vol. 8, Nos. 1 & 2, Mary Ann Liebert, Inc.
Sennerby, L. et al., Early tissue response to titanium implants inserted in rabbit cortical bone, Journal of Materials Science: Materials in Medicine, 1993, pp. 240-250, vol. 4, Chapman & Hall.
Tozman, E.C. et al., Adverse Reactions With Oral and Parenteral Gold Preparations, Medical Toxicology, 1987, pp. 177-189, vol. 2, ADIS Press Limited.
Yanni, G. et al., Intramuscular gold decreases cytokine expression and macrophage numbers in the rheumatoid synovial membrane, Annals of Rheumatic Diseases, 1994, pp. 315-355, vol. 53, Published by group.bmj.com.
Office Action, dated Aug. 25, 2013, issued by the Danish Patent and Trademark Office in counterpart Danish Application No. PA 2013 70007.
Pedersen, D.S. et al., Metallic gold slows disease progression, reduces cell death and induces astrogliosis while simultaneously increasing stem cell responses in an EAE rat model of multiple sclerosis, Histochemistry and Cell Biology Journal, Jul. 22, 2012, pp. 787-802, Springer-Verlag.

* cited by examiner

MICRON-SIZED GOLD, KIT COMPRISING SAID GOLD AND ITS USE AS A NON-TOXIC IMMUNE SUPPRESSOR

FIELD OF THE INVENTION

The present invention relates to sterile micron-sized gold particles or flakes contained in capped vials, kit of part comprising said vial and a commercial product of capable of suspending the particles or flakes, as well as their preparation and use in suppressing inflammation and pain. The invention also relates to gold coated implants that can be applied together with the sterile micron sized gold particles according to the first aspect.

BACKGROUND

Inflammation is part of the complex biological response of vascular tissues to harmful stimuli, such as pathogens, damaged cells, or irritants. Prolonged inflammation, known as chronic inflammation, leads to a progressive shift in the type of cells present at the site of inflammation and is characterized by simultaneous destruction and healing of the tissue from the inflammatory process. Chronic inflammation can also lead to a host of diseases, such as hay fever, periodontitis, atherosclerosis, rheumatoid arthritis, and even cancer. The autoimmune disorders are different of types disorders of the immune system caused by overactive immune responses. The immune system fails to properly distinguish between self and non-self, and attacks part of the body.

Treatment of rheumatic diseases with gold salts, the so-called gold cure, is an old technique but is still widely used and accepted as a rational treatment of patients who do not respond satisfactorily to the new anti-inflammatory and anti-rheumatic drugs. Like glucocorticoids, injectable gold salts have also shown therapeutic benefits in the treatment of e.g. bronchial asthma. Although the underlying mechanisms have never been fully unraveled, it is known that gold ions alter the function of macrophages by inhibiting their lysosomal enzymes and lowering their production of pro-inflammatory cytokines (Persillin and Schiff 1966; Yanni et al 1994, Nieminen R et al. 2010). Furthermore, gold ions have been shown to inhibit the transcriptionfactor Nuclear Factor-kappaB (NF-kB) (Ligacheva et al. 2012).

It is suggested in U.S. Pat. No. 4,784,991 to use metal salts and in particular gold hyaluronate for the treatment of joint inflammation by administering the salt intra-articularly. In addition, it is disclosed in U.S. Pat. No. 4,746,504 that heavy metal salts of hyaluronic acid, in particular silver, gold, cerium and tungsten salts of hyaluronic acid have also proven to be useful as antimicrobial agents indirectly adding to the effect as an anti-inflammatory reagent. Authorized and scientifically well-founded use of gold in rheumatoid arthritis is mainly performed with various gold-thio compounds such as gold sodium thiomalate such as Myocrisin® available from Aventis Pharma.

Use of gold implants has also been described for the treatment of inflammatory diseases. In WO 02/094294 the metal is implanted or applied locally and provided with a radially enlarged free surface to ensure the greatest possible contact with the affected epithelial tissue. Using autometallography (AMG) it has been shown that from such implants gold ions are liberated in vivo and in vitro (Larsen et al. 2007, Danscher 2002, Danscher and Stoltenberg 2006). The process most likely involves a macrophage-induced reorganization of the biofilm which is created on the metallic surface immediately after an implant is placed in the organism (Larsen et al 2007; see also Sennerby et al 1993; Futami et al 2000; Roach et al 2007). The fact that the released atoms are taken up by cells that trigger the immune response i.e. macrophages and mast cells has initiated intense basic and clinical research projects aimed at revealing whether a sufficient amount of metallic gold can be released from gold implants to implement it in the medical and veterinarian practice as a nontoxic suppressor of local inflammation, i.e. a safe local gold cure.

From e.g. U.S. Pat. No. 7,655,261 it is known to implant distributed metallic gold pieces for example having a diameter of ≥20 μM in a patient to cure or alleviate a plurality of various diseases and conditions. The total surface area of these gold pieces is greater than the surface area of one implanted piece of gold with the same total weight. In U.S. Pat. No. 7,655,261 it is also proposed that the gold pieces be distributed as an open or closed gilding on a support medium for reducing inflammation and stop/suppress release of toxic metal ions from the implant into the body.

The use of gold compounds in medicine has been limited due to adverse effects. Both parenterally and perorally administered gold compounds (i.e. gold salts) can cause pronounced nephrotoxicity because of the intense presence of gold ions in the blood following injection of e.g. Aurothiomalate and careful monitoring is needed when administering the traditional gold compounds (Tozman and Gottlieb 1987; Felson et al 1990). These toxic effects can be by-passed by using local application of metallic gold implants and micro implants i.e. gold particles.

Therefore, it is an object of the present invention to provide a kit, a medical device and methods for improved treatment of immune disorders and cosmetic treatment using gold. It is also an object to provide means and methods for upholding long termed osseointegration.

SUMMARY OF THE INVENTION

With this background, it is an object of the present invention in one aspect to provide a kit comprising a capped vial and a liquid contained in a syringe, the capped vial being penetrateable by the syringe, wherein the capped vial comprises solid micron-sized gold and at least one glass bead, wherein the liquid is compatible with the human body and is capable of maintaining the micron sized gold particles in suspension for at least one minute at a temperature of approximately 25° C.

The kit provides means for preparing a medical device or medicament that can be administered directly into an afflicted area or an area that would benefit from such administration and hence ensuring proper localization of the micron sized gold particles to the area in question. The at least one glass bead facilitates the suspension and distribution of the particles in the vial. Thus, by suspending the solid metal gold particles in a vehicle compatible with living tissue in humans and animals a bolus of solid metal gold particles is extremely easy to apply locally and targeted.

It is an important aspect that the liquid is capable of maintaining the gold in suspension at least for a minute in order to allow proper administration of the combination without precipitation of the gold. This affects both the efficiency of the treatment i.e. the gold is held in suspension until administered which ensures proper administration to the correct location and at the same time the treatment is more cost effective since the gold does not precipitate and remain in the syringe or container, that is waste is minimized.

It is contemplated that the micron-sized solid gold can be shaped as particles or flakes.

In a particular embodiment the micron-sized gold is flakes. Since the density of gold flakes will most likely be lower than that of gold particles, in addition flakes will often have a larger surface area than particles with the same minimum dimension of 20 µm as claimed. Thus, when flakes are used the liquid can have a viscosity in the lower range without the effect of the treatment is compromised. Moreover, since the weight is lower the treatment also comes with a lower cost.

Thus, in a particular embodiment, when the micron-sized gold is a particle the diameter of the micron-sized solid gold is above 20 µm. In a more preferred embodiment, the diameter of the micron-sized solid gold is in the range 20 µm to 150 µm, preferably between 20 µm and 45 µm.

When the micron-sized solid gold is flakes the length of the largest dimension. That is the length of the largest dimension is in a particular embodiment above 20 µm. In a more preferred embodiment, the length of the largest dimension is in the range 20 µm to 150 µm, preferably between 20 µm and 45 µm.

The size and shape of the micron-sized solid gold particles or flakes provides a surface area for direct contact with the patient's tissue and the lower limit ensures that the released metal ions are not phagocytosed/engulfed by macrophages with resulting phagocytosis of the particles. Also, the upper range limit of 150 µm is important for a balance between suspension of the particles and surface area available. Thus, if the particles or flakes are too heavy proper suspension may be compromised.

In a further embodiment, the viscosity of the liquid is in the range of 1-150 cP or 1-150 mPa·s (1 mPa·s=1 cP) at a temperature of 25° C. In a more preferred embodiment the viscosity of the liquid 8-50 cP more preferred 15-50 cP at a temperature of 25° C., and in one example the viscosity is 5 cP at a temperature of 25° C.

The high viscosity of the liquid ensures that the micron-sized solid gold particles or flakes, having a high density, are maintained in suspension for a sufficient time in the liquid. When using flakes the viscosity may be in the lower range without compromising the suspensibility. Preferably, the liquid is medical grade hyaluronic acid commercial medical grade hyaluronic acid can be obtained under the trade name Suplasyn®, from Bioniche Pharma, Galway, Ireland; and DisCoVisc® from Alcon Laboratories Inc. Texas, USA. The concentration of hyaluronic acid in saline water can be any suitable concentration. The choice of concentration is within the skill of the art and is most suitably a commercially available product. An example of commercially available hyaluronic acid which is suitable in the present invention is 10 mg/ml.

In particular, when the size of the micron-sized solid gold is particles or is in the range of 20 µm to 55 µm the viscosity of the liquid is approximately 50 cP at a temperature of 25° C.

In another particular embodiment when the micron-sized solid gold is flakes is in the range of 20 µm to 55 µm the viscosity of the liquid is approximately 1-4 cP at a temperature of 25° C.

The kit is designed so that the micron sized gold particles or flakes are present in an amount which is sufficient for treating a condition only once, i.e. due to the size and amount of gold and the speed of the bio-released gold ions one administration is sufficient for a given troubled location.

In a particular embodiment the capped vial comprises between 2 and 100 mg micron-sized solid gold particles or flakes, preferably between 5 and 50 mg, more preferred between 8 and 10 mg, and in one example, the capped vial comprises approximately 10 mg micron-sized solid gold particles.

The capped vial is also provided as an intermediate product for the preparation of the medical device or medicament the capped vial comprises solid micron-sized gold particles or flakes and at least one glass bead, wherein the smallest diameter of the micron-sized solid gold particles is above 20 µm, more preferred in the range 20 µm to 150 µm or the length of the largest dimension of the flakes is above 20 µm, more preferred in the range 20 µm to 150 µm.

It is also contemplated that the capped vial comprises between 2.5 and 100 mg micron-sized solid gold particles or flakes; more preferred approximately 10 mg micron-sized solid gold particles or flakes. Further, the specific combination of a vial comprising between 2.5 and 100 mg micron-sized solid gold particles or flakes, more preferred approximately 10 mg micron-sized solid gold particles or flakes wherein the smallest diameter of the micron-sized solid gold particles is above 20 µm, more preferred in the range 20 µm to 150 µm or the length of the largest dimension of the flakes is above 20 µm, more preferred in the range 20 µm to 150 µm provides an intermediate for a medical device or medicament according to the invention which medical device or medicament is sufficient to provide lifelong treatment of a condition described herein with one single administration thereby enhancing patient compliance.

In yet another embodiment the liquid is medical grade hyaluronic acid which is characterized by having a high viscosity and purity.

In another aspect of the invention is provided a medical device or medicament for the treatment of inflammatory diseases, the medical device or medicament being obtainable by a method comprising the steps of providing a capped vial comprising solid micron-sized gold particles or flakes and at least one glass bead, preferably having a diameter of 3-8 mm, injecting a liquid which is compatible with the human body and which liquid is capable of maintaining the micron-sized gold particles in suspension for at least 1 minute, into the capped vial, agitating the mixture of solid micron-sized gold particles or flakes, glass bead(s) and the injected liquid to provide a suspension, whereby the glass beads facilitates efficient distribution of the micron-sized solid gold particles or flakes in the suspension, preferably for 30 seconds when the vial has a temperature of 20-40° C., more preferred of 25-30° C.

aspirating the suspension into the syringe, whereby the medical device or medicament is provided said medical device or medicament being the solid micron-sized gold particles or flakes in suspension.

In one embodiment the liquid has a viscosity in the range of 1-110 cP, more preferred 5-50 cP, such as 20, 30 40 or 50 cP, and preferably the liquid is medical grade hyaluronic acid.

In another embodiment the diameter of the micron-sized solid gold particles is above 20 µm, more preferred in the range 20 µm to 150 µm, such as in the range 20-50 µm, 30-60 µm, 40-70 µm, 20-80 µm, 30-90 µm, or approximately below 100 µm, below 110 µm, below 120 µm, below 130 µm or below 140 µm or any combination.

In yet another embodiment the length of the largest dimension of the micron-sized solid gold flakes is above 20 µm, more preferred in the range 20 µm to 150 µm, such as in the range 20-50 µm, 30-60 µm, 40-70 µm, 20-80 µm, 30-90 µm, or approximately below 100 µm, below 110 µm, below 120 µm, below 130 µm or below 140 µm or any combination.

Hyaluronic acid is a widespread natural element of the mammalian body HA and is readily metabolized by natural reactions without causing any negative side effects, which leaves the solid metal gold particles at the site of administration. Thus, the compatible liquid is accepted by the immune system and the suspended well distributed solid metal gold particles will be attacked by macrophages that initiate a dissolucytotic process which causes release of gold ions. Said gold ions cause the local suppression of inflammation and pain which is recognized in the art when administered as gold salts.

Thus, the medical device or medicament according to the present invention, when injected, is capable of providing a surprisingly significant, effective and long lasting immune suppression without the side effects known in the art, such as nephrotic overload.

The capped vial comprises between 2.5 and 100 mg micron-sized solid gold particles; more preferred approximately 10 mg micron-sized solid gold particles. This ensures a dosage sufficient for a single administration.

In a third aspect is provided a medical device or medicament for use in the treatment of inflammatory diseases, wherein the inflammatory disease is selected from the group consisting of e.g. arthrose, multiple sclerosis, Alzheimer's disease, psoriasis, eczema, autoimmune diseases and/or inflammation related conditions, such as wounds, as well as cosmetic conditions such as wrinkles.

In yet another aspect of the invention is provided a method for treating an inflammatory disease or a cosmetic condition comprising the steps of administering a therapeutically effective amount or an effective amount of a medical device or medicament as described above into a location in need of treatment, preventative or cosmetic treatment. It is preferred that the medical device or medicament is administered once. It is also contemplated that the medical device or medicament is a cosmetic composition.

It is preferred that the location in need of treatment or preventative treatment is selected from the vicinity of a joint, intra-articularly, subcutaneously (e.g. fillers), intra-sclerally the urinary bladder, injuries/trauma i.e. sites injured by a lesion or eczema and along a sutured wound.

A method for preparing the medical device or the medicament is also provided such as a method described in the leaflet preferably accompanying the kit or the capped vial. The method comprises the steps of providing a capped vial comprising solid micron-sized gold particles or gold flakes, such as micron-sized solid gold particles where the diameter of the micron-sized solid gold particles is above 20 µm, more preferred in the range 20 µm to 150 µm or the length of the largest dimension of the gold flakes is above 20 µm, more preferred in the range 20 µm to 150 µm, and at least one glass bead, such as 1, 2 or 3 glass beads, said glass beads preferably having a diameter of 3-8 mm;

injecting a liquid which is inert to the human body and which liquid is capable of maintaining the micron sized gold particles or gold flakes in suspension for at least 1 minutes, into the capped vial, wherein the liquid is selected from hyaluronic acid, collagen, pharmaceutically acceptable silicones and the like;

agitating the mixture of the solid micron-sized gold particles or flakes, glass bead(s) and the injected liquid to provide a suspension, whereby the glass beads facilitates efficient distribution of the micron-sized solid gold particles or flakes in the suspension, such as agitating for at least 30 seconds when the vial has a temperature of 20-40° C., more preferred 20-40° C. even more preferred 25-30° C.

aspirating the suspension into the syringe, whereby the medical device is provided said medical device being the solid micron-sized gold particles or flakes in suspension.

Thereafter the medical device is suitable for administration in an area in need of treatment.

In another aspect is provided an implant for human or animal use said implant having an anchor part to be in contact with bone tissue and a non-anchor part to be in contact with adjacent tissue characterised in that the surface of both parts of the implant is at least partly coated with gold. Metallic gold specs on the anchor part will ensure that inflammation between implant and bone is suppressed, securing the mechanical fixation of the implant. Gilding of the entire anchor part was found to compromise the long term fixation of the implant.

Gold specs or gilding of the non-anchor part ensures that inflammation will be suppressed and release of toxic metals from the implant to the surrounding connective tissue is minimal.

A number of studies have tested application of gold in various forms to implants in order to reduce inflammation and secure long termed mechanical fixation. Hence, for example it was shown in Zainali et al, (J Biomed Mater Res A. 2009) that gilding of the entire implant resulted in poor fixation and that further studies of dose response was necessary. In Zainali et al 2010 (Wiley Periodicals) application of gold separate from the implant was tested but no effect on fixation and inflammation was shown. Here it was suggested to reduce the amount of gold added.

It has now unexpectedly been found that it is an advantage to reduce the amount of gold specifically in the anchor part of the implant facing the bone tissue as this will not influence the mechanical fixation and endow the bone-implant zone with anti-inflammatory properties.

Hence, it is not the amount of gold as such but the specific location of gold on the implant that has proven the beneficial effect. The fact that the amount of gold as such has no effect was also shown in the test of Zainali et al. 2013 (*J Biomed Res A*. January 2013) where only half of the implant was gilded. This test did not show the beneficial effect of the invention.

In one embodiment the surface of the gold coated implant is coated with gold dots. It is contemplated that the gold coating layer covers no more than 70% of the total surface of the anchor part to be in contact with bone tissue, more preferred 0-50%, such as 10%, 15%, 20%, 25%, 30%, 35%, 40%, 45%, and 60%.

It is further contemplated that the layer of gold has a thickness in the range of 50-500 nm, more preferred in the range 100-200 nm, even more preferred 100-100 nm, such as 150, 300, or 400 500 nm. Larger thicknesses are contemplated but from an economical perspective the thickness should not be more than 500 nm without losing the effect.

In yet another aspect of the invention the gold coated implant is obtained by a method comprising the steps of a. immersing the implant in a strong alkaline solution b. cleaning the implant by cathodic polarization to produce a hydrogen gas at the surface of the implant comprising sodium hydroxide, c. immersing the implant in a weak acid solution d. applying a layer of gold to the implant by immersing the non-anchor part of the implant into a weak acid gold bath comprising gold cyanide; and e. applying points of gold particles or flakes to the anchor part of the implant, and f. rinsing the implant between each step of a-d.

In another embodiment the gold coated implant is used in a method for improving long term mechanical fixation of an implant, comprising the steps of applying a dose of a gold particle or flake, wherein the biggest dimension of micron-sized solid gold particles or flakes is in the range 20 µm to 75 µm to an inflicted tissue; and inserting the gold coated implant, where the implant having an anchor part to be in contact with bone and the remaining surface to be facing adjacent tissue characterised in that the non-anchor part to be facing adjacent tissue has a larger total area covered in gold than the anchor part to be in contact with bone.

Accordingly it was found that by supplementing the gilding of the anchor part of the implant with the micro implants provided according to the first aspect of the invention, the overall recovery was improved. Hence it was found contrary to Zainali et al 2010 that when applying the gold particles as supplement to the gold coated implant a significant effect was observed.

In a presently one embodiment, the dose is applied using a kit comprising a capped vial and hyaluronic acid contained in a syringe, said capped vial being penetrateable by the syringe, wherein the capped vial comprises solid micron-sized gold, wherein the biggest dimension of the micron-sized solid gold particles or gold flakes in the range 20 µm to 75 µm, and at least one glass bead.

By combining the insertion of the partially gold coated implant along with gold particles or gold flakes in proper suspension into the inflicted tissue may result in a more effective reduction of, or complete inhibition of the immune response of the fibrous tissue around the implant and at the same time avoid osteolysis.

In addition, a method for improving therapy for the treatment and prevention of inflammatory diseases is provided, wherein the improvement comprises delivering to a human or animal in need of such treatment a gold coated implant, wherein the method comprising the steps of applying a dose of a gold particle or flake where the biggest dimension of micron-sized solid gold particles or flakes is in the range of 20 microns to 75 microns to the implant tissue; and wherein the implant having at least one part of its surface to be in contact with bone and the remaining surface to be facing adjacent tissue characterised in that the remaining surface to be facing adjacent tissue has a larger total area covered in gold than the at least one part of the surface to be in contact with bone.

In one embodiment, the disease is rheumatoid arthritis.

It is contemplated that all features and embodiments can be combined for each aspect of the invention.

DETAILED DESCRIPTION OF THE INVENTION

The invention will now be described in greater details below.

The micron sized gold particles according to the present invention have a purity of 99.99% w/w pure gold. Gold particles according to the invention are available from for example Hildebrand & Cie SA, Thônex-Genève, Suisse.

The size of the gold particles is selected so that the diameter or largest cross-section of a solid metal gold piece is at least 20 µm, separated by sieving through sieves having the appropriate mesh size.

When the micron-sized gold is above this size it is not phagocytosed by macrophages.

In the context of the present invention the term dissolucytosis, is an extracellular liberation of gold ions from the surface of gold particles bigger than 20 microns. Such particles are particles that cannot be phagocytozed by macrophages. The dissolution membrane makes it possible for the macrophages to control the chemical milieu at the gold surface and the dissolucytosis of gold ions is most likely caused by the capacity of the macrophages to manipulate releasing cyanide ions and altering the oxygen tension and the pH in their vicinity (Larsen et al. 2006; Ferre and Claria 2004). The process of dissolucytosis is limited by the size of the gold surface, the amount of dissolucytotic macrophages, and their state of activity. The slow speed of the process results in a limited liberation of gold ions taken up solely by cells close to the implant, while inflammation will cause a dramatic increase in the amount of bio-released gold ions, that later decline to the 'at rest' stadium.

Dissolucytosis, the bio-release of gold ions by adhering macrophages, can only take place if the particles stay outside the cells, i.e. are not phagocytized as the dissolucytotic release takes place only extracellularly. Therefore the lower range of 20 micron is an important aspect for an efficient treatment.

In the context of the present invention the liquid capable of maintaining micron-sized gold particles in suspension is any liquid capable of carrying the gold particles or flakes in any embodiment described herein for at least 1 minute. In terms of parameters the liquid may be characterized by its viscosity as the liquid must be relatively viscous if gold particles have to be suspended while gold flakes can be suspended by less viscous solutions having a viscosity close to the viscosity of water.

In the context of the present invention "liquid" is contemplated as being either a concentrated liquid or a solution of a compound such as an aqueous solution.

When the micron sized gold are particles the viscosity of the liquid is preferably in the range 1-150 cP, more specifically 40-110 cP, such as approximately 50 cP at 25° C. An example is DisCoVisc® mentioned above.

The liquid may be selected from e.g. collagen, silicones or cellulose that are compatible with the human body, such as medical grade silicones, hyaluronic acid as well as derivatives and combinations thereof. It is also contemplated that the liquid includes but is not limited to fluids extracted from the recipient him-/herself and other constituents forming part of the human and animal body. It is contemplated that any of the above can be used in concentrated form or in solution such as in an aqueous solution.

Hyaluronic acid is a presently preferred liquid. It is a glycosaminoglycan (GAG) composed of disaccharides chains, composed of D-glucuronic acid and D-N-acetylglucosamine, linked together via alternating β-1,4 and β-1,3 glycosidic bonds. Hyaluronic acid is distributed widely throughout for example connective, epithelial, neural tissues and is the major component of the synovia (Korenek et al. 1992).

Approximately, one third of hyaluronic acid in a human is degraded and synthesized every day. Thus, hyaluronic acid is ubiquitous in human and animal tissues, where it exhibits significant structural, rheological and physiological functions.

According to the invention hyaluronic acid is contemplated in all forms such as free acid and any pharmaceutically acceptable salt, ester or hydrate thereof. An example of salt derivatives of the acid is selected from but not restricted to sodium and potassium as well as salts of heavy metals as described in e.g. U.S. Pat. No. 4,746,504, U.S. Pat. No. 4,784,991 and U.S. Pat. No. 601,790.

It is contemplated that throughout the description and claims when hyaluronic acid or hyaluronate is mentioned it is contemplated that any form of the above is covered. It is also contemplated in any suitable concentration such as 10 mg/ml in 0.9% saline water. Hyaluronic acid, also called hyaluronan, is manufactured in large scale in physiological acceptable molarities and is commercial available as a medical device for injection in joints, eyes, skin (fillers), ventricular system in the brain, the urinary bladder and more. Hyaluronic acid suitable in the present invention is available for example under the trade name Suplasyn® available from Bioniche Pharma, Ireland.

Typically hyaluronic acid/hyaluronane is available as an 8-10 mg/ml physiological aqueous solution, but in the context of the present invention solutions in the range 5-15 mg/ml is suitable, such as 10 mg/ml.

The glass beads according to the invention have a size compatible with a commercial available capped vial. In preferred embodiments the glass beads have a diameter of 3 to 8 mm. The size of the glass beads should be chosen so that proper agitation or mixing and distribution of the particles in the liquid can be obtained.

The capped vial according to the invention is any suitable vial, but most traditional are commercially available Eppendorf® 4 ml vials. Other vials are equally applicable. The size depends on the location to be treated and the corresponding amount of liquid and gold. The specific choice of the vial is a trivial choice which is within the skill of the art.

The syringe comprising the liquid contemplates any syringe suitable of holding a liquid and penetrating a capped vial. Numerous syringes are available in the art such as the pre-filled syringes used in commercial hyaluronic products sold under the trade name the Suplasyn® and Provisc® or any other suitable syringe.

For the purpose of the medical device or medicament and the methods of the invention it is contemplated that the syringe is prefilled or filled on the site, from e.g. a 10 ml or 25 ml capped vial of hyaluronic acid, before injecting into the capped vial.

The amount of gold in the vial can be any amount. From an economic perspective the amount should however be minimized as much as possible without loosing clinical efficiency. It is preferred that the amount is sufficient to provide a lifelong supply of gold ions, at a specific location in the human or animal body once the medicament/medical device is administered. Thus, in most application the amount of gold in the vial is in the range 2 to 16 mg, more preferred 6-14 mg, even more preferred 8-12 mg, such as 10 mg. For suspending an amount effective and economical in a lifelong local treatment the amount of liquid could be in the range 1-5 ml, depending of the circumstances. A suitable amount depends on the amount of gold suspended and is within the skill of the art.

When the micron-sized gold is particles the ratio between gold and liquid is in the range 2-100 mg/1 ml.

When the micron-sized gold is flakes the ratio between gold and liquid is in the range 1-100 mg/1 ml.

The invention also relates to an implant such as prostheses, stents, hearing aids and the like which may be made from titanium alloys, zirconium alloys, or ceramics, or any other implant with a gold gildable surface.

Various applications of gold are possible in the method of the present invention. For example, gold may be applied to the surface of an implant by gilding, amalgamating, patching, or dotting. The method of applying the gold to an implant is within the skill of the art.

In the context of the present invention the terms medical device and medicament are used interchangeably. The terms cover the gold particles or flakes suspended in the liquid according to the invention. Neither of the terms should be interpreted narrowly. The compositions of the invention may be seen as both medical devices and medicaments as they constitute compositions capable of treating the human body. Whether denoted medical device or medicament/medicinal products depend on the legislation under which they are approved. It is also contemplated that the medical device or medicament is denoted cosmetic composition when applied for this purpose.

The disorders that can be treated according to the invention are selected from but not limited to inflammatory disease selected from the group consisting of e.g. arthrose, multiple sclerosis, Alzheimers disease, psoriasis, eczema, autoimmune diseases and inflammation related conditions, such as wounds, as well as cosmetic conditions such as wrinkles.

The experiments described below illustrate the invention in more details.

EXAMPLES

Example 1—Therapeutic Effect of the Invention

Experimental Procedures
Test Animals

In a study by Pedersen et al. (2012), 8-week-old rats were used to evaluate the release of gold ions from gold particles suspended in hyaluronic acid. The animals were housed under standard conditions, i.e. a 12-hour light/dark cycle at 22° C., and with free access to food and water. All experimental procedures were performed in accordance with Danish law. The experimental animals were injected with 2× 2.72 mg metallic gold suspended in sodium hyaluronate into 1) 20 neocortex 2) brain ventricles. The controls were injected hyaluronate only. The study showed a slowing of disease progression in terms of reduced weight loss in gold-treated animals as compared to vehicle-treated animals demonstrating the effect of therapy.

Solid Metal Gold Particle Treatment

Ninety-nine percent pure metallic gold (Alfa-Aesar,Ge) was sieved using 2 aluminum sieves (Retsch, Ge) to obtain solid metal gold particles in the size of 20 to 45 µm. 463 mg solid metal gold particles was mixed with 0.85 ml sodium hyaluronate (10 mg/ml in physiological water, i.e. 0.9% saline), Provisc®, Alcon, in a water bath set at 40° C.

Prior to the injections, the animals were anesthetized with an injection of a mixture of Narcoxyl-vet (Xylazin) and Ketominal-vet. The deeply anesthetized animals were placed in a Benchmark stereotaxic instrument (myNeuroLab.com, USA) and a longitudinal incision was made in the skin covering the skull. Two drill holes were made under the microscope according to the Paxinos-Franklin coordinates, and the solid metal gold sodium hyaluronate/sodium hyaluronate injections were given in the center of each drill hole.

Autometallography (AMG)

The AMG developer consists of a 60 ml gum arabicum solution (Bidinger, Aarhus, DK) and 10 ml sodium citrate buffer (23.5 g sodium citrate (Merck 6448, VWR, DK) to 100 ml distilled water), 15 ml reducing agent (0.85 g of hydroquinone (Merck 4610, VWR, DK) dissolved in 15 ml distilled water at 40° C.), and 15 ml solution containing silver ions (0.12 g silver lactate (Fluka 85210 supplied by Sigma-Aldrich, Vallensbk, DK) in 15 ml distilled water at 40° C.); the latter is added immediately before use while thoroughly stirring the AMG solution. The AMG development takes place in a water bath at 26° C. for 60 to 15 min under a dark hood. Development is stopped by replacing the developer with a 5% thio-sulphate solution for 10 min. Finally, the tissue sections/slices are rinsed several times in distilled water (for details see Danscher 1981 and Danscher & Stoltenberg 2006). Tissue slices to be analyzed in the light or electron microscope were treated in accordance with the following two procedures, respectively.

Fixation and Tissue Processing for AMG

After transcardial perfusion with 3% glutaraldehyde (Merck 4239, VWR, Albertslund, DK) the brains was immediately removed from the body and allowed to post-fixate in the same fixative.

For light microscopical analyses the slices were placed in a 30% solution of sucrose until they sank to the bottom of the glass. The slices were then frozen with $CO_2$, placed in a cryostat, and allowed a temperature fall to −17° C. After AMG development (see below), the sections were counterstained with a 0.1% solution of aqueous toluidine blue (pH 4.0), dehydrated in ascending concentrations of alcohol and xylene, embedded in DePex and covered with a cover glass. For electron microscopy the slices were cut on a vibratome and the resulting 100-μm-thick sections were developed in AMG. The areas to be analyzed were cut out, placed in osmium tetroxide (1% in phosphate buffer for 30 minutes) and embedded in Epon.

From these Epon blocks, 3 μm-thick sections were cut and AMG developed. One of the three sections on each glass slide was counterstained with toluidine blue. After LM analysis, the sections to be analyzed further in the electron microscope were re-embedded in top of an Epon block. Ultrathin sections were cut, placed on a grid and counterstained with uranyl citrate and lead acetate (Danscher 1981; Danscher and Stoltenberg 2006).

Light microanalysis of AMG developed sections showed fine traces of liberated gold ions in tissue near the metal gold deposit within the region of the lesion and its border zone. In this area, cytoplasmatic accumulation of silver enhanced nanogold particles, resulting from the bio-released gold ions taken up by the cells, was seen in both glia cells and neurons. The AMG technique for demonstration gold ions bound to macromolecules in the tissue relay on reduction of the gold ions (by radiating the sections with UV light) to metallic gold atoms that accumulate in nanoparticles. It is these particles, originating from the bio-released gold ions that are made visible by AMG silver enhancement. At ultrastructural levels the AMG enhanced nanogold particles were found to be located in lysosome-like organelles. The number of gold labeled lysosomes was sparse as was the amount of AMG grains in each lysosome. All control sections were void of AMG staining. Gold particles placed in the ventricular system of the brain showed dissolucytotic release of gold ions into the cerebrospinal fluid and were taken up by glia cells around the ventriculocisternelle system.

Results—Gold Tracing

Based on these observations it is shown that a safe local gold cure can be obtained by using small but non-phagocytizable i.e. >20 μm gold particles hereby limiting any damaging effects of the injection of the gold particles, and investigations in our laboratory indicates that placing micron-sized solid metal gold particles/implants within the ventricular system is a feasible way to circumvent placing the pure gold metal directly in the brain tissue. The amount of gold ions liberated through dissolucytosis has shown to be so limited and localized that even micron-sized gold particle could serve as a life-long cure with a minimal risk of toxic side effects.

The increased number and activity of microglia/macrophages during an ongoing inflammation will automatically increase the amount of gold ions liberated when it is most needed. The hyaluronic acid injections have no observable influence on the brain (Gorm Danscher and Agnete Larsen "*Effects of dissolucytotic gold ions on recovering brain lesions*" Histochem Cell Biol (2010) 133:367-373. Bio-liberated gold ions i.e. gold ions dissolucytotically liberated by macrophages by gold particles influence the immunological response by affecting the cells that are involved in the inflammatory process (Larsen A et al., 2008; Pedersen MØ et al., 2009 "Metallic gold reduces TNFalpha expression, oxidative DNA damage and pro-apoptotic signals after experimental brain injury"; Pedersen MØ et al., 2010; Pedersen MØ et al., 2009, "*Metallic gold treatment reduces proliferation of inflammatory cells, increases expression of VEGF and FGF, and stimulates cell proliferation in the subventricular zone following experimental traumatic brain injury*"; Pedersen D S et al., 2012).

These findings indicates that treatment with metallic gold implants with a large surface 'in casu' gold particles, is an approach with clinical dimensions for ameliorating aseptic inflammation and pain everywhere in the body, including in the brain. Furthermore, the treatment is believed to have protective and regenerative potentials as shown in the mouse brain.

REFERENCES

Aktas O, Ullrich O, Infante-Duarte C, Nitsch R, Zipp F (2007) Neuronal damage in brain inflammation. *Arch. Neurol.* 64, 185-189.

Aschner M, Sonnewald U, Tan, K H (2002) Astrocyte modulation of neurotoxicity. *Brain Pathol.* 12, pp. 475-481.

Danscher G Localization of gold in biological tissue. (1981) "A photochemical method for light and electron microscopy". *Histochemistry* 71, pp. 81-88.

Danscher G "In vivo liberation of gold ions from gold implants". (2002) Autometallographic tracing of gold in cells adjacent to metallic gold. *Histochem. Cell Biol.* 117, pp. 447-15 452.

Danscher G, Stoltenberg M Autometallography (AMG). (2006) Silver enhancement of quantum dots resulting from (1) metabolism of toxic metals in animals and humans, (2) in vivo, in vitro and immersion created zinc-sulphur/zinc-selenium nanocrystals, (3) metal ions liberated from metal implants and particles. *Prog. Histochem. Cytochem.* 41, 57-139.

Felson D T, Anderson J J, Meenan R F (1990) The comparative efficacy and toxicity of second-line drugs in rheumatoid arthritis. Results of two metaanalyses. *Arthritis Rheum.* 34, 134-213.

Ferre N, Claria, J (2006) New insight into the regulation of 30 liver inflammation and oxidative stress. *Mini Rev. Med. Chem.* 6, 1321-1330.

Futami, T, Ohnishi H, Taguchi N, Kusakari H, Oshima H, Maeda T (2000) Tissue response to titanium implants in the rat maxilla: ultrastructural and histochemical observations of the bone-titanium interface. *J. Periodontol.* 71, 287-298.

Larsen A, Kolind K, Pedersen D S, Doering P, Pedersen M O, Danscher G, et al (2008) Gold ions bio-released from metallic gold particles reduce inflammation and apoptosis and increase the regenerative responses in focal brain injury. Histochem Cell Biol. 130(4): 681-92.

Larsen A, Stoltenberg M. & Danscher, G (2007) In vitro liberation of charged gold atoms. Autometallographic tracing of gold ions released by macrophages grown on metallic gold surfaces 128, 1-6 Histochem Cell Biol.

Mhatre M, Floyd R A, Hensley, K. (2004) Oxidative stress and neuroinflammation in Alzheimer's disease and amylotrophic lateral sclerosis: common links and potential therapeutic targets. *J. Alzheimer Dis.* 6, 147-157.

Pedersen M O, Larsen A, Pedersen D S, Stoltenberg M, Penkowa M. (2009) Metallic gold reduces TNFalpha expression, oxidative DNA damage and pro-apoptotic signals after experimental brain injury. 0. Brain Res 19; 1271:103-13.

Pedersen MØ, Larsen A, Stoltenberg M, Penkowa M. (2010) Bio-released gold ions modulate expression of neuroprotective and hematopoietic factors after brain injury. Brain Res. 2010 Jan. 11; 1307:1-13.

Pedersen MØ, Larsen A, Pedersen D S, Stoltenberg M, Penkova M. (2009) Metallic gold treatment reduces proliferation of inflammatory cells, increases expression of VEGF and FGF, and stimulates cell proliferation in the subventricular zone following experimental traumatic brain injury. Histol Histopathol 24(5):573-86.

Pedersen D S, Fredericia P M, Pedersen M O, Stoltenberg M, Penkowa M, Danscher G, Rungby J, Larsen A (2012). Metallic gold slows disease progression, reduces cell death and induces astrogliosis while simultaneously increasing stem cell responses in an EAE rat model of multiple sclerosis. Histochem Cell Biol. 138(5):787-802. Epub 2012 Jul. 22.

Persellin R H, Ziff, M. (1966) The effect of gold salt on lysosomal enzymes of the peritoneal macrophage. *Arthritis Rheum.* 9, 57-65.

Potashkin J A, Meredith G E (2006) The role of oxidative stress in the dysregulation of gene expression and protein metabolism in neurodegenerative disease. *Antoxid. Redox Signal* 8, 144-151.

Roach P., Eglin, D, Rohde K, Perry C C (2007) Modern 20 biomaterials: a review—bulk properties and implications of surface modifications. *J. Mater. Sci. Mater. Med.* 18, 12631277.

Sennerby L, Thomsen, P, Ericson L E (1993) Early tissue response to titanium implants inserted in rabbit cortical bone. *J. 25 Mater. Sci. Mater. Med.* 4, 494-502.

Tozman E C, Gottlieb, N L (1987) Adverse reactions with oral and parenteral gold preparations. *Med. Toxicol.* 2, 177-189.

Yanni, G., Nabil, M., Farahat, M. R., Poston, R. N. & Panayi, G. S. Intramuscular gold decreases cytokine expression and macrophage numbers in the rheumatoid synovial membrane. Ann. Rheum. Dis. 53, 315.

Zainali K, Danscher G, Jakobsen T, Baas J, Møller P, Bechtold J E, Soballe K (2013) Assessment of modified gold surfaced titanium implants on skeletal fixation. J Biomed Mater Res A. 2013 January; 101(1):195-202 [first online publication 30 Jul. 2012].

The invention claimed is:

1. A kit comprising a capped vial and a liquid contained in a syringe, said capped vial being penetrateable by the syringe,
   wherein the capped vial comprises solid micron-sized gold particles or gold flakes,
   wherein a biggest dimension of the solid micron-sized gold particles or gold flakes is in a range of 20 μm to 75 μm, and at least one glass bead,
   wherein the liquid is compatible with the human body and is capable of maintaining the solid micron-sized gold particles or gold flakes in suspension for at least one minute at a temperature of approximately 25° C.,
   wherein the capped vial comprises between 5 and 10 mg of the solid micron-sized gold particles or gold flakes.

2. A kit according to claim 1, wherein a viscosity of the liquid is in a range of 1-110 cP.

3. Kit according to any of the claim 1, wherein the liquid is medical grade hyaluronic acid.

4. Medical device, for the treatment of inflammatory diseases, said medical device being obtainable by a method comprising the steps of
   providing a capped vial comprising solid micron-sized gold particles or gold flakes and at least one glass bead having a diameter of 3-8 mm,
   injecting a liquid which is inert to the human body and which liquid is capable of maintaining the solid micron-sized gold particles or gold flakes in suspension for at least 1 minutes,
   agitating the mixture of the solid micron-sized gold particles or gold flakes, the at least one glass bead and the injected liquid to provide a suspension, whereby the at least one glass beads facilitates efficient distribution of the solid micron-sized gold particles or gold flakes in the suspension,
   aspirating the suspension into the syringe, whereby the medical device is provided said medical device being the solid micron-sized gold particles or gold flakes in suspension,
   wherein the capped vial comprises between 5 and 10 mg of the solid micron-sized gold particles or gold flakes.

5. Medical device according to claim 4, wherein the liquid has a viscosity in a range of 1-110 cP.

6. Medical device according to claim 4, wherein the liquid is medical grade hyaluronic acid.

7. A capped vial comprising solid micron-sized gold particles or gold flakes and at least one glass bead,
   wherein a smallest diameter of the micron-sized solid gold particles or gold flakes is above 20 μm, and
   wherein the capped vial comprises between 5 and 10 mg of the solid micron-sized gold particles or gold flakes.

8. Medical device according to claim 4 use in the treatment of inflammatory diseases.

9. Medical device according to claim 8, wherein the inflammatory disease is selected from a group consisting of arthrose, multiple sclerosis, Alzheimer's disease, psoriasis, eczema, autoimmune diseases and inflammation related conditions, wounds, as well as cosmetic conditions such as wrinkles.

10. A kit according to claim 1, wherein the viscosity of the liquid is in a range of 15-50 cP at a temperature of approximately 25° C.

11. Medical device according to claim 4, wherein the liquid has a viscosity in a range of 15-110 cP at a temperature of approximately 25° C.

12. A kit according to claim 1, wherein a smallest diameter of the solid micron-sized gold particles or gold flakes is above 20 μm.

13. Medical device according to claim 4, wherein a smallest diameter of the solid micron-sized gold particles or gold flakes is above 20 μm.

\* \* \* \* \*